US012208089B2

(12) United States Patent
Habash

(10) Patent No.: US 12,208,089 B2
(45) Date of Patent: Jan. 28, 2025

(54) ADJUSTING EXPRESSION LEVEL OF A GENE ENCODING A SIRTUIN PROTEIN BY TREATING A HUMAN SUBJECT WITH A NITROXIDE

(71) Applicant: Louis Habash, Irvine, CA (US)

(72) Inventor: Louis Habash, Irvine, CA (US)

( * ) Notice: Subject to any disclaimer, the term of this patent is extended or adjusted under 35 U.S.C. 154(b) by 0 days.

(21) Appl. No.: 17/330,143

(22) Filed: May 25, 2021

(65) Prior Publication Data

US 2022/0378765 A1    Dec. 1, 2022

(51) Int. Cl.
  *A61K 31/445*   (2006.01)
(52) U.S. Cl.
  CPC .................................. *A61K 31/445* (2013.01)
(58) Field of Classification Search
  CPC .................................................... A61K 31/445
  See application file for complete search history.

(56) References Cited

U.S. PATENT DOCUMENTS

| | | | | |
|---|---|---|---|---|
| 5,352,442 | A | 10/1994 | Proctor | |
| 5,462,946 | A | 10/1995 | Mitchell et al. | |
| 6,096,759 | A * | 8/2000 | Wilcox | A61K 31/445 514/315 |
| 7,153,866 | B1 * | 12/2006 | Mitchell | A61K 31/42 514/315 |
| 8,778,969 | B2 * | 7/2014 | Proctor | A61P 31/22 514/315 |
| 9,101,619 | B2 * | 8/2015 | Habash | A61P 5/50 |
| 9,314,457 | B2 * | 4/2016 | Gibson | A61K 31/45 |
| 9,522,143 | B2 * | 12/2016 | Habash | A61P 3/10 |
| 9,522,144 | B2 * | 12/2016 | Habash | A61K 31/445 |
| 9,545,398 | B1 * | 1/2017 | Habash | A61K 31/445 |
| 9,579,311 | B1 * | 2/2017 | Habash | A61K 31/445 |
| 9,700,550 | B1 * | 7/2017 | Habash | A61K 31/445 |
| 9,744,162 | B1 * | 8/2017 | Habash | A61K 31/445 |
| 9,937,162 | B2 * | 4/2018 | Gibson | A61P 9/00 |
| 10,064,852 | B2 * | 9/2018 | Habash | A61K 31/445 |
| 10,159,665 | B2 * | 12/2018 | Habash | A61K 31/445 |
| 10,231,959 | B2 * | 3/2019 | Habash | A61K 31/445 |
| 10,245,256 | B2 * | 4/2019 | Habash | A61K 31/445 |
| 10,441,568 | B2 | 10/2019 | Goldstein et al. | |
| 10,441,578 | B2 * | 10/2019 | Habash | A61K 31/445 |
| 10,828,291 | B2 * | 11/2020 | Habash | A61K 45/06 |
| 10,874,654 | B2 * | 12/2020 | Habash | A61K 31/445 |
| 11,324,737 | B1 * | 5/2022 | Habash | A61P 31/00 |
| 11,510,913 | B1 * | 11/2022 | Habash | A61P 25/00 |
| 2008/0319014 | A1 * | 12/2008 | Habash | A61P 5/50 514/315 |
| 2009/0209581 | A1 * | 8/2009 | Habash | A61P 37/02 514/315 |
| 2012/0046314 | A1 * | 2/2012 | Habash | A61P 35/00 514/315 |
| 2018/0078538 | A1 * | 3/2018 | Habash | A61K 31/445 |
| 2019/0224178 | A1 * | 7/2019 | Habash | A61K 31/445 |
| 2019/0224179 | A1 * | 7/2019 | Habash | A61K 45/06 |

OTHER PUBLICATIONS

Tang et al. Circulation, Nov. 21, 2017, vol. 136, No. 21, pp. 2051-2067 (Year: 2017).*
Soule et al. Free Radical Biology & Medicine, 2007, vol. 42, pp. 1632-1650 (Year: 2007).*
Yamamoto et al. Molecular Endocrinology, 2007, vol. 21, No. 8, pp. 1745-1755 (Year: 2007).*
Machado de Oliveira et al. Frontiers in Pharmacology, May 2012, vol. 3, Article 82, 9 pages (Year: 2012).*
Teena et al. Biomolecules, 2020, 10, 1466; doi:10.3390/biom10101466, 16 pages (Year: 2020).*
Yu et al. J. Neurochem., 2016, vol. 137, pp. 371-383 (Year: 2016).*
Rizzi et al. International Journal of Cardiology, 2013, vol. 165, pp. 165-173 (Year: 2013).*
Ritchie et al. Journal of Molecular and Cellular Cardiology, 2007, vol. 42, pp. 1119-1128 (Year: 2007).*
Negrini et al. Nature Reviews Molecular Cell Biology, 2010, vol. 11, pp. 220-228 (Year: 2010).*
Oliveira (Journal of Neurochemistry, 2010, vol. 114, pp. 1-12) (Year: 2010).*
Kitada et al. Frontiers in Endocrinology, Mar. 2019, vol. 10, article 187, 12 pages (Year: 2019).*
Martinez-Jimenez et al. (Diabetes Metab. Syndr. Jan.-Feb. 2019;13(1):582-589; Epub Nov. 10, 2018) (Year: 2019).*
Hiratsuka et al. (Biochemical and Biophysical Research Communications, 2003, vol. 309, p. 558-566) (Year: 2003).*
Kitada, et al., Sirtuins and Type 2 Diabetes: Role in Inflammation, Oxidative Stress, and Mitochondrial Function. Front. Endocrinol., Mar. 27, 2019 | https://doi.org/10.3389/fendo.2019.00187.
Sarikhan et al. "SIRT2 deacetylase represses NFAT transcription factor to maintain cardiac homeostasis." The Journal of biological chemistry vol. 293,14 (2018): 5281-5294. doi:10.1074/jbc.RA117. 000915.
Lantier et al. SIRT2 knockout exacerbates insulin resistance in high fat-fed mice. PloS one vol. 13,12 e0208634. Dec. 11, 2018, doi:10. 1371/journal.pone.0208634.
Park, et al., SIRT2 is a tumor suppressor that connects aging, acetylome, cell cycle signaling, and carcinogenesis. Translational Cancer Research, (2012); 1(1), 15-21. DOI: 10.3978/j.issn.2218-676X.2012.05.01.
De Oliveira, et al. "SIRT2 as a Therapeutic Target for Age-Related Disorders." Frontiers in pharmacology vol. 3 82. May 3, 2012, doi: 10.3389/fphar.2012.00082.
Zhang, et al. "The Clinical Significance of SIRT2 in Malignancies: A Tumor Suppressor or an Oncogene ?. " Frontiers in oncology vol. 10 1721. Sep. 8, 2020, doi:10.3389/fonc.2020.01721.

(Continued)

*Primary Examiner* — James D. Anderson
(74) *Attorney, Agent, or Firm* — Knobbe, Martens Olson & Bear LLP

(57) ABSTRACT

Some embodiments disclosed herein include a method for increasing an expression level of a gene. The methods include administering an effective amount of a nitroxide antioxidant to a human subject having a decreased expression level of SIRT2, whereby expression level of the gene is increased.

14 Claims, No Drawings

(56) References Cited

OTHER PUBLICATIONS

Wang, et al. "Downregulation of SIRT2 by Chronic Stress Reduces Expression of Synaptic Plasticity-related Genes through the Upregulation of Ehmt2." Experimental neurobiology vol. 28,4 (2019): 537-546. doi:10.5607/en.2019.28.4.537.

Donato et al., Mechanisms of Dysfunction in the Aging Vasculature and Role in Age-Related Disease, Circulation Research, Sep. 14, 2018, vol. 123, pp. 825-848.

Yu et al., High glucose-induced oxidative stress represses sirtuin deacetylase expression and increases histone acetylation leading to neural tube defects, Journal of Neurochemistry, 2016, vol. 137, Iss. 3, pp. 371-383.

International Search Report and Written Opinion for PCT/US2022/030066 issued Sep. 1, 2022.

\* cited by examiner

ADJUSTING EXPRESSION LEVEL OF A GENE ENCODING A SIRTUIN PROTEIN BY TREATING A HUMAN SUBJECT WITH A NITROXIDE

BACKGROUND

Field

The present disclosure relates generally to the field of modulation of gene expression and more particularly to increasing expression levels of one or more genes relating to Sirtuin 2 by treating human subjects with a nitroxide.

Description of the Related Art

Diseases and conditions are treatable by adjusting the expression levels and activities of key genes in the body. Gene expression irregularities, whether overexpressed, activated, under expressed or inhibited underlie the development and progression of diseases and conditions. Some diseases are characterized by deficient expression of certain genes while other diseases result from over expression of certain genes. A disease resulting from irregular gene expression can be prevented, treated, or reversed by administering a nitroxide antioxidant to target and correct the expression levels of the genes.

Expression levels of genes are often naturally controlled in an appropriate way, but sometimes natural control of gene expression fails. For example, in cancer, genes providing instructions for cell growth are activated or switched on, when they should be off. Autoimmune diseases and aging are other examples of diseases and conditions that result from irregular gene expression. As cells age, the natural control of gene expression deteriorates promoting several diseases and conditions such as inflammation, chronic pain, infections, neurodegenerative disease, neurological disorders, skin diseases, etc. It is essential to identify the irregular expression of the genes involved in the cause of the disease and adjust the expression levels of those genes.

Often referred to as gene therapy, the targeting and correction of cellular dysfunction through adjusting the expression level of certain genes is necessary to prevent, treat, or reverse a disease or condition. Only by identifying key genes and developing therapeutics that altering the expression patterns of those genes can we prevent the development of the disease, reduce its effects once it has occurred, or reverse it all together.

One key family of genes involved in several diseases and conditions is the sirtuin gene family and associated genes. When these genes are underexpressed it results in several diseases and conditions associated with the underexpression of the gene. Thus, correction of the underexpression of sirtuin genes is essential for treatment and prevention of the associated diseases and conditions.

SUMMARY

Some embodiments disclosed herein provide methods for increasing or activating gene expression. The methods, in some embodiments, include identifying a human subject over the age of 35 and having a decreased expression level of SIRT2; and administering to the human subject an effective amount of a nitroxide antioxidant resulting in a increased expression level of the gene. In some embodiments, the gene is SIRT2. In some embodiments, the human subject is over the age of 20. In some embodiments, the human subject is over the age of 45. In some embodiments, the human subject is over the age of 55. In some embodiments, the human subject is over the age of 65. In some embodiments, the expression level of the gene in a skin tissue is increased by treatment. In some embodiments, the expression level of the gene in an adipose tissue is increased by treatment. In some embodiments, the expression level of the gene in blood is increased by treatment. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for increasing the expression level of a gene in a human subject in need thereof, comprising: identifying a human subject having a decreased expression level of SIRT2; administering to the human subject an effective amount of a nitroxide antioxidant, whereby the expression level of SIRT2 is increased. In some embodiments, the gene is SIRT2. In some embodiments, the decreased expression level of the gene is age-related. In some embodiments, the human subject is over the age of 35. In some embodiments, the human subject is over the age of 45. In some embodiments, the human subject is over the age of 55. In some embodiments, the human subject is over the age of 65. In some embodiments, the decreased expression level of the gene is disease-related. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the disease is age-related. In some embodiments, the expression level of the gene in a skin tissue is increased by treatment. In some embodiments, the expression level of the gene in an adipose tissue is increased by treatment. In some embodiments, the expression level of the gene in blood is increased by treatment with the nitroxide antioxidant. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for reducing risk of a disease in a human subject in need thereof, comprising: identifying a human subject over the age of 35 having an increased risk of a disease due to an decreased expression level of SIRT2; administering to the human subject an effective amount of a nitroxide antioxidant, whereby the expression level of SIRT2 is increased. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is SIRT2. In some embodiments, the human subject is over the age of 45. In some embodiments, the human subject is over the age of 55. In some embodiments, the human subject is over the age of 65. In some embodiments, the expression level of the gene in a skin tissue is increased by treatment. In some embodiments, the expression level of the gene in an adipose tissue is increased by treatment. In some embodiments, the expression level of the gene in blood is increased by treatment. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing a cancer and in need of an increased expression level of a SIRT2 gene; administering to the human subject an effective amount of a nitroxide antioxidant, whereby the expression level of the gene associated with sirtuin proteins and sirtuin protein activity is increased. In some embodiments, the cancer can be selected from the group consisting of bladder cancer, colorectal cancer, hepatocellular carcinoma, prostate carcinoma, and kidney carcinoma. In some embodiments, the gene is SIRT2. In some embodiments, the cancer is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased by treatment. In some embodiments, the expression level of the gene in an adipose tissue is increased by treatment. In some embodiments, the expression level of the gene in blood is increased by treatment. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing an autoimmune disease and in need of an increased expression level of a SIRT2 gene; administering to the human subject an effective amount of a nitroxide antioxidant, wherein the expression level of the gene associated with sirtuin proteins and sirtuin protein activity is increased. In some embodiments, the autoimmune disease can be selected from the group consisting of rheumatoid/osteoid arthritis, systemic lupus erythematosus (SLE), inflammatory bowel disease, multiple sclerosis, atherosclerosis, and osteoporosis. In some embodiments, the gene is SIRT2. In some embodiments, the autoimmune disease is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased by treatment. In some embodiments, the expression level of the gene in an adipose tissue is increased by treatment. In some embodiments, the expression level of the gene in blood is increased by treatment. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for a disease associated with a decreased expression level of sirtuin proteins and sirtuin protein activity is increased in a patient in need thereof, comprising: identifying a human subject having or at risk of developing a disease associated with a decreased expression of SIRT2; administering to the human subject an effective amount of a nitroxide antioxidant, whereby the expression level of SIRT2 is increased. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is SIRT2. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased by treatment. In some embodiments, the expression level of the gene in an adipose tissue is increased by treatment. In some embodiments, the expression level of the gene in blood is increased by treatment. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual over the age of 35 in need of an increased expression level of SIRT2; and administering to the individual an effective amount of a nitroxide antioxidant to increase the level of expression of the gene associated with sirtuin proteins and sirtuin protein activity. In some embodiments, the gene is SIRT2. In some embodiments, the human subject is over the age of 45. In some embodiments, the human subject is over the age of 55. In some embodiments, the human subject is over the age of 65. In some embodiments, the human subject has a decreased expression level of the gene. In some embodiments, the individual has or is at risk of developing an age-related condition. In some embodiments, the age-related condition comprises decreased senescence in a tissue. In some embodiments, the age-related condition comprises inhibition sirtuin proteins and sirtuin protein activity in a tissue. In some embodiments, the age-related condition comprises increased molecular heterogeneity. In some embodiments, the age-related condition comprises increased functional impairment in a tissue. In some embodiments, the expression level of the gene in a skin tissue is increased by treatment. In some embodiments, the expression level of the gene in an adipose tissue is increased by treatment. In some embodiments, the expression level of the gene in blood is increased by treatment. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual having a disease-related decreased expression level of SIRT2; and administering to the individual an effective amount of a nitroxide antioxidant to increase the level of expression of the gene associated with sirtuin proteins and sirtuin protein activity. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is SIRT2. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased by treatment. In some embodiments, the expression level of the gene in an adipose tissue is increased by treatment. In some embodiments, the expression level of the gene in blood is increased by treatment. In some embodiments, the expression level of the gene in a neuronal tissue is increased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with sirtuin proteins and sirtuin protein activity is increased. In some embodiments, the individual has an decreased expression level of the gene. In some embodiments, the gene is SIRT2. In some embodiments, the condition is an age-related condition. In some embodiments, the age-related condition comprises increased senescence in a tissue. In some embodiments, the age-related condition comprises underactivation of SIRT2 in a tissue. In some embodiments, the age-related condition comprises increased molecular heterogeneity. In some embodiments, the age-related condition comprises increased functional impairment in a tissue. In some embodiments, the age-related condition is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the human subject is over the age of 35. In some embodiments, the human subject is over the age of 45. In some embodiments, the human subject is over the age of 55. In some embodiments, the human subject is over the age of 65.

Some embodiments disclosed herein provide methods for increasing the expression level of a gene in a human subject in need thereof, comprising: identifying a human subject having a decreased expression level of SIRT2; and delivering to the human subject an effective amount of a nitroxide antioxidant to increase the level of expression of the gene associated with sirtuin proteins and sirtuin protein activity. In some embodiments, the nitroxide antioxidant is 4-hydroxy-2,2,6,6-tetramethylpiperidine-1-oxyl. In some embodiments, the decreased expression level of the gene is age-related. In some embodiments, wherein the decreased expression level of the gene is cancer-related. In some embodiments, the decreased expression level of the gene is disease-related. In some embodiments, the decreased expression level of the gene is neurodegeneration-related. In some embodiments, the decreased expression level of the gene is infection related. In some embodiments, the increased the level of expression of the gene improves sirtuin activity and mitochondrial function. In some embodiments, the expression level of the gene is increased in a tissue selected from the group consisting of a skin tissue, an immune tissue, an adipose tissue, a pancreatic tissue, cardiac tissue, and a neuronal tissue by treatment.

Some embodiments disclosed herein provide methods for increasing an expression level, in an eukaryotic cell, of one or more genes encoding sirtuin proteins involved in mitochondrial sirtuin by contacting the eukaryotic cell with a nitroxide antioxidant. In some embodiments, the one or more genes is SIRT2. In some embodiments, the nitroxide antioxidant is 4-hydroxy-2,2,6,6-tetramethylpiperidine-1-oxyl. In some embodiments, the eukaryotic cell is a cancer cell. In some embodiments, the expression level of the one or more genes is decreased in said cell in a tissue selected from the group consisting of a skin tissue, an immune tissue, an adipose tissue, a pancreatic tissue, cardiac tissue, and a neuronal tissue. In some embodiments, prior to said contacting, the eukaryotic cell exhibits an age-related decreased expression level of said one or more genes. In some embodiments, prior to said contacting, the eukaryotic cell exhibits a disease-related decreased expression level of said one or more genes. In some embodiments, prior to said contacting, the eukaryotic cell exhibits a neurodegeneration-related expression level of said one or more genes.

Some embodiments disclosed herein provide methods for improving chemotherapeutic response in a human subject comprising: contacting cancer cells in the subject with an effective amount of a nitroxide antioxidant whereby a level of expression of sirtuin proteins and sirtuin protein activity is increased in said cancer cells. In some embodiments, said cancer cells are known to have decreased SIRT2 function. In some embodiments, the decreased expression level of one or more genes following treatment initiates apoptosis within one or more of said cancer cells. In some embodiments, the decreased expression level reduces or prevents resistance to other chemotherapeutic agents. In some embodiments, the nitroxide antioxidant is 4-hydroxy-2,2,6,6-tetramethylpiperidine-1-oxyl. In some embodiments, the gene is selected from the group consisting of SIRT2.

Some embodiments disclosed herein provide methods for increasing sirtuin proteins and sirtuin protein activity in a human subject comprising: identifying a human subject known to have decreased SIRT2 function; and delivering to the subject an effective amount of a nitroxide antioxidant, whereby a level of sirtuin proteins and sirtuin protein activity is increased. In some embodiments, the nitroxide antioxidant is 4-hydroxy-2,2,6,6-tetramethylpiperidine-1-oxyl. In some embodiments, decreased SIRT2 function is age-related. In some embodiments, the decreased SIRT2 function is cancer-related. In some embodiments, the decreased SIRT2 function is disease-related. In some embodiments, the decreased SIRT2 function is neurodegeneration-related. In some embodiments, the decreased SIRT2 function is infection-related. In some embodiments, the decreased level of expression of the gene improves remodeling of damaged tissues. In some embodiments, the expression level of the gene is decreased in a tissue selected from the group consisting of a skin tissue, an immune tissue, an adipose tissue, a pancreatic tissue, cardiac tissue, and a neuronal tissue following treatment.

Some embodiments disclosed herein provide methods for treating a human subject having cancer comprising: delivering an effective amount of a nitroxide antioxidant to a human subject, wherein the human subject has previously been administered at least one chemotherapeutic agent, whereby a level of expression of sirtuin proteins and sirtuin protein activity is increased. In some embodiments, the human subject having cancer is identified with a decreased expression of SIRT2. In some embodiments, the methods further comprise administering a promotor of a SIRT2 to the human subject.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means the detection of a gene product that is expressed or produced by a nucleic acid molecule by standard molecular biology methods, which gene product refers to e.g. an unspliced RNA, an mRNA, a splice variant mRNA, a polypeptide, a post-translationally modified polypeptide, a splice variant polypeptide etc., and specifically products made using an RNA gene product as a template, e.g. cDNA of the RNA.

As used herein, "differential expression" of a gene means that the expression of the gene is at a higher level ("increased expression") or lower level ("decreased expression") in a human subject suffering from a disease, for example cancers and autoimmune diseases. Differential expression includes both quantitative, as well as qualitative, differences in the temporal or cellular expression pattern in a gene or its expression products among, for example, normal and diseased cells, or among cells which have undergone different disease events or disease stages.

As used herein, "increasing the expression level" of a gene means causing the expression of the gene to decrease by treating the human subject with a compound, for example a nitroxide antioxidant, such that the expression level of the gene after treatment is lower than the expression level of the gene before treatment in the human subject.

As used herein, "delivering" a compound shall mean bringing that compound into contact with a relevant cell, tissue, or organism. Similarly, "contacting" shall mean that the compound contacts a relevant target, such as a tissue or cell or tumor. In either case, delivery or contact in an organism can be affected by directly administering the compound to the organism, or by administering a different compound to the organism, such as a prodrug that is converted in vivo to the desired compound. In short, these terms cover any action that leads to contact between the desired compound and a target cell, tissue, or organism.

The present disclosure describes methods of modulating gene expression in human subjects. However, this is illustrative only and not intended to be limiting. For example, the methods disclosed herein can be used for modulating gene expression in other vertebrates, such as but not limited to mammals, birds, reptiles, fish, and the like (with modifications wherein appropriate). Mammals and birds include most agricultural animals. Treatment of companion animals, e.g., dogs, cats, or birds is also contemplated.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Human Subject Identification

The present disclosure relates to methods of treating alterations in gene expression, such as age-related, cancer-related, disease-related, neurodegeneration-related, and infection-related alteration in gene expression. Gene expression changes also play important roles in aging and serve as biomarkers of physiological decline and disease conditions, such as neurodegenerative diseases, and cancers. Therefore, one aspect of the present disclosure is methods of treating a human subject having an age-related, cancer-related, disease-related, neurodegeneration related, and/or infection-related decrease in gene expression levels, such as those genes associated with sirtuin proteins and sirtuin protein activity. In some embodiments, the human subject can be identified based on the human subject's age, gene expression level, family history, health conditions, medical history, habits, or a combination thereof.

Regardless of the cause of the downregulation, some common terminology can be used. In some embodiments, the expression level of a gene (e.g., SIRT2) in a human subject is considered to be downregulated or decreased if the decrease in the expression level of that gene is statistically significant compared to that of a control or a reference. In some embodiments, the expression level of a gene (e.g., SIRT2) in a human subject is considered to be upregulated or increased after a treatment if the increase in the expression level of that gene is statistically significant. The control or reference can be, for example, a normal healthy population, a population at large, a collection of individuals of the same age or condition or sex, or the same human subject at a different time (e.g., at an earlier time of life when the human subject does or does not have the disease or condition that results in the downregulation).

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The increase in expression level can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the increase in expression level can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the increase in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the human subject may have an age that is, is about, or is over 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of SIRT2. Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

Genes Associated With Sirtuin Proteins and Sirtuin Protein Activity

In some embodiments, administering to the human subject an effective amount of the nitroxide antioxidant results in an increased expression level of a gene, for example SIRT2. Therefore, some embodiments disclosed herein provide methods for treating an individual in need thereof, comprising identifying an individual having a disease-related decreased expression level of SIRT2; and administering to the individual an effective amount of a nitroxide antioxidant to increase the level of expression of SIRT2. Some embodiments disclosed herein provide methods for treating an individual in need thereof, comprising identifying an individual in need of an increased expression level of a SIRT2 gene; and administering to the individual an effective amount of a nitroxide antioxidant to increase the level of expression of SIRT2. Some embodiments disclosed herein provide methods for treating an individual in need thereof, comprising: administering to the individual, known to have a disease-related decreased expression level of SIRT2, an effective amount of a nitroxide antioxidant to increase the level of expression of SIRT2. Some embodiments disclosed herein provide methods for treating an individual in need thereof, comprising: administering to an individual, known to be in need of an increased expression level of a SIRT2 gene, an effective amount of a nitroxide antioxidant to increase the level of expression of sirtuin proteins and sirtuin protein activity.

In addition to increasing the expression of SIRT2, administration of the nitroxide antioxidant may result in an increase to one or more of sirtuin 1 (SIRT1), sirtuin 2 (SIRT2), sirtuin 3, (SIRT3), sirtuin 4 (SIRT4), sirtuin 5 (SIRT5), sirtuin 6, (SIRT6), and sirtuin 7 (SIRT7). While the sirtuin genes may be ubiquitously expressed throughout several different body tissues, research has provided particular insight into identified locations and functions. For example, SIRT1 has been found expressed in the nucleus of cells and interacts with PGC-1α, FOXOs, NFκB to confer impact on functions such as metabolism, inflammation, and neurodegeneration SIRT2 has been identified throughout several different types of tissue and can be readily found in the cell cytoplasm. SIRT2 has been known to interact with H4, α-tubulin and other cellular components or genes to regulate numerous different cellular functions such as Cell cycle and tumorigenesis. SIRT3 has been found in a the nucleus and mitochondria of cells. It is known to interact with AceCS2 to impact metabolism. SIRT4 has been identified in cellular mitochondria and interacts with ADP-ribosyl transferase and GDH to regulate Insulin secretion. SIRT5 has also been found in the mitochondria. SIRT6 impacts DNA repair and has been identified in the Nucleus of cells to interact with ADP-ribosyl transferase and DNA polymerase β. SIRT7 is also in the nucleus and interacts with RNA polymerase I for rDNA transcription. Non-limiting examples of diseases associated with altered level of sirtuin proteins and sirtuin protein activity include cancer; breast cancer; lung cancer; kidney cancer; cancers of the ovary and uterus; cancer of the central nervous system; cancers of the head and neck; melanoma; lymphomas; leukemia; neurological disorders; Alzheimer's disease; Parkinson's disease; Huntington's disease; amyotrophic lateral sclerosis; stroke; cardiovascular disorders; ischemia; heart failure; infections, infectious diseases; bacterial infections; inflammatory responses; viral infections; autoimmune diseases; systemic lupus erythematosus; autoimmune lymphoproliferative syndrome; rheumatoid arthritis; and thyroiditis.

The genes associated with sirtuin proteins can be SIRT1, SIRT2, SIRT3, SIRT4, SIRT5, SIRT6, SIRT7, or a homologue thereof. For example, the treatment results in increased expression levels of SIRT2. The increased expression level of SIRT2, increases sirtuin proteins and sirtuin protein. The increased level of SIRT2 results in a decrease in or disappearance of signs and symptoms of a disease associated with decreased SIRT2 function, including the curing of the disease associated with decreased SIRT2 function. In some embodiments, the increased expression level of SIRT2, increases the level of sirtuin proteins and sirtuin protein activity. The increased level of sirtuin proteins and sirtuin protein activity results in a decrease in or disappearance of signs and symptoms of the disease associated with decreased SIRT2 function, including the curing of the disease associated with decreased SIRT2 function. In some embodiments, the increased level of sirtuin proteins and sirtuin protein activity inhibits, suppress, prevent, or reverse the disease or the symptoms associated with the disease.

Molecular Disease Profiles

The development and progression of all disease results from a dysfunction of one or more genes involved in the biological processes associated with a disease or condition. Traditionally, a diagnosable disease or condition required a patient to present with a symptom of the disease. This approach fails to consider the underlying cause of cellular dysfunction that resulted in the symptom. In this way, current therapeutic strategies are generally ineffective regarding the treatment of a cause of the disease because they fail to target and correct the dysfunction of the genes that cause the disease. Instead, a disease is best defined by the identifying the dysfunctional gene that causes the disease and correcting the expression level of that gene to a healthy state.

The human genome is comprised of over 20,000 genes and each of them provide instructions necessary for the formation and function of proteins. Genes are the foundation of all cellular composition and function. They contain provide all necessary instruction for the healthy function and formation of proteins. Every component of a cell exists and operates based on the instruction provided by genes, and each cell communicates and interacts with each other to form tissues and control the healthy function of the human body. Even extracellular molecules are created and released based on the expression levels of genes controlling the formation and release from the cell. Certain biological processes rely on extracellular molecules to engage cell-surface receptors that transmit a signal into the cell and every step of this process is controlled by the genes associated with that biological process. While biological processes may be complicated, gene expression provides a fundamental ability to focus on the precise cause of a switch from healthy biological activity to a disease state.

Every disease and condition can be traced back to a dysfunction in one or more genes that prevents their ability to maintain a healthy state for an individual. One of the most common dysfunctions related to the expression level of a gene. Genes are expressed in a regulated manner to control the amount of instruction they provide. The quantity of gene expression correlates with the quantity of proteins formed within a cell, as well as modulates the activity of each protein.

Overexpression of a gene causes diseases by overproducing proteins and increasing the activity of the proteins which leads to signs and symptoms identifiable as a disease. Conversely, when a gene is underexpressed, the encoded proteins are reduced and their functions are inhibited resulting in diminished function of the cell and identifiable characteristics of a disease.

In a healthy state, genes are expressed in a regulated manner that maintains or promotes healthy function of the cell. When a gene is inappropriately expressed, the cell may try to compensate by upregulating or downregulating other genes. However, the cell cannot maintain compensatory mechanisms indefinitely and the cell will eventually succumb to the disease state caused by the inappropriate gene expression, that can result in nearby cells being affected in a similar way. In order to treat or prevent a disease or condition, the underlying dysfunction of the genes must be identified and corrected by modulating the gene expression to a healthy state.

Diseases and conditions exploit gene dysfunctional expression to advance the disease by regulating cellular function to promote the needs of the disease state occurring within the cell. Cells survive by maintaining a state of healthy homeostasis. The sirtuin family of genes is directly responsible for regulating elements of homeostasis from cellular metabolism to mitosis. Each of the sirtuin genes is responsible for providing instructions to the cell including interacting with other master genes such as NRF2, HIF1a, and NFKb. By controlling the activation of these genes, the sirtuin gene family can promote healthy cell division, oxidative stress management, preventing carcinogenesis, preventing heart diseases, and maintaining proper neurological function.

When the sirtuin genes are downregulated, the activity of the genes are inhibited and overall function is reduced. This leads to increased oxidative stress, dysregulation of NFKb activity, reduced NRF2 activation and severe downstream consequences that cause diseases such as cancer, heart disease, neurological disorders, and the disease of aging. Where a disease is caused by the decreased expression and decreased activity of the sirtuin family of genes, it is imperative to target these genes and increase their expression levels. Without support from a treatment that can effectively increase the expression level of these genes, the associated disease will continue and advance to destroying the cell in the process.

Certain conditions, such as cardiovascular diseases, diabetes, obesity, and aging are associated with (e.g., causes or caused by) underexpression of sirtuin protein encoding genes resulting in the inhibition, inactivity, and disfunction of vital cellular processes within cells and tissues. Thus, increasing the expression level of the sirtuin family of genes is essential for treatment and prevention of certain conditions.

Siturin Gene Family

Sirtuin enzymes have originally been defined as a family of nicotinamide adenine dinucleotide-dependent enzymes that deacetylate lysine residue on various proteins. Certain sirtuins have in addition an ADP-ribosyltransferase activity. The sirtuins are remarkably conserved throughout evolution from archaebacteria to eukaryotes. Mammalian sirtuins SIRT1-SIRT7 are implicated in a variety of cellular functions ranging from gene silencing, over the control of the cell cycle and apoptosis, to energy homeostasis. On a whole-body level, the wide range of cellular activities of the sirtuins indicate that they constitute therapeutic targets to combat several different diseases such as metabolic, neurodegenerative, and proliferative diseases. Each disease treated by increasing expression level of the siturin genes is based on the impact of a treatment such as administration of a nitroxide antioxidant to increase the expression level of the sirtuin gene. (Hiroyasu Yamamoto, Kristina Schoonjans, Johan Auwerx, Sirtuin Functions in Health and Disease, Molecular Endocrinology, Volume 21, Issue 8, 1 Aug. 2007, Pages 1745-1755).

While the sirtuin genes may be ubiquitously expressed throughout several different body tissues, research has provided particular insight into identified locations and functions. For example, SIRT1 has been found expressed in the nucleus of cells and interacts with PGC-1α, FOXOs, NFκB to confer impact on functions such as metabolism, inflammation, and neurodegeneration SIRT2 has been identified throughout several different types of tissue and can be readily found in the cell cytoplasm. SIRT2 has been known to interact with H4, α-tubulin and other cellular components or genes to regulate numerous different cellular functions such as Cell cycle and tumorigenesis. SIRT3 has been found in a the nucleus and mitochondria of cells. It is known to interact with AceCS2 to impact metabolism. SIRT4 has been identified in cellular mitochondria and interacts with ADP-ribosyl transferase and GDH to regulate Insulin secretion. SIRT5 has also been found in the mitochondria. SIRT6 impacts DNA repair and has been identified in the Nucleus of cells to interact with ADP-ribosyl transferase and DNA polymerase β. SIRT7 is also in the nucleus nucleus and interacts with RNA polymerase I for rDNA transcription. (Yamamoto, 2007).

SIRT2

SIRT2 gene encodes a member of the sirtuin family of proteins, homologs to the yeast Sir2 protein. Members of the sirtuin family are characterized by a sirtuin core domain and grouped into four classes. The protein encoded by this gene is included in class I of the sirtuin family. Several transcript variants are resulted from alternative splicing of this gene. Only transcript variants 1 and 2 have confirmed protein products of physiological relevance. A leucine-rich nuclear export signal (NES) within the N-terminal region of these two isoforms is identified. Since deletion of the NES led to nucleocytoplasmic distribution, it is suggested to mediate their cytosolic localization.

SIRT2 is localized in both the cytoplasm and nucleus, and it is widely expressed in various tissues, including the brain, muscle, pancreas, liver, kidney, and adipose tissues. SIRT2 interacts with many histone and non-histone protein substrates, including tubulin and histone H4. SIRT2 is involved in multiple cellular functions, including genomic integrity, cell growth, differentiation, and energy metabolism, and reduced SIRT2 activity has been implicated in cancer, neurodegeneration and metabolic diseases. Previous studies have demonstrated that SIRT2 plays an important role in various physiological processes in maintaining metabolic homeostasis, including inflammation, oxidative stress and mitochondrial function, as well as adipocyte differentiation, fatty acid oxidation, gluconeogenesis, and insulin sensitivity. A few reports have shown that SIRT2 exerts anti-inflammation and antioxidative stress effects and improves mitochondrial function in metabolic-related tissues, such as skeletal muscle. (Sirtuins and Type 2 Diabetes: Role in Inflammation, Oxidative Stress, and Mitochondrial Function. Munehiro Kitada, Yoshio Ogura, Itaru Monno and Daisuke Koya. Front. Endocrinol., 27 Mar. 2019).

Regulation of Inflammation: SIRT2 regulates inflammation by deacetylating the NF-κB p65 subunit, similar to SIRT1. Pais et al. demonstrated that SIRT2 plays a crucial role as a major inhibitor of microglia-mediated inflammation and neurotoxicity through the deacetylation of NF-κB (p65). In other experimental inflammatory disease models, the anti-inflammatory effect of SITR2 has been demonstrated through the suppression of the NF-κB signaling pathway. However, further studies are necessary to elucidate whether this anti-inflammatory effect of SIRT2 may be exerted in metabolic diseases, including insulin resistance and T2DM. (Kitada, 2019).

Regulation of Oxidative Stress: SIRT2 regulates redox homeostasis in cells. SIRT2-dependent deacetylation of FOXO3a leads to increased expression of Mn-SOD to improve oxidative stress. In addition, glucose-6-phosphate dehydrogenase (G6PD) is a key enzyme in the pentose phosphate pathway (PPP) and plays a crucial role in the oxidative stress response by producing nicotinamide adenine dinucleotide phosphate (NADPH) and reduced form glutathione (GSH), the main intracellular reductant. Wang et al. reported that SIRT2 activates G6PD through deacetylation on lysine 403 in G6PD, which plays an important role in maintaining the cellular redox status and protecting cells from oxidative damage. (Kitada, 2019).

SIRT2 deacetylates nuclear factor-κB p65 subunit [NF-κB], resulting in decreased expression of inflammatory mediators. Sirt2 also induces Mn-SOD expression by deacetylating Forkhead box protein O3a (FOXO3a). Additionally, SIRT2 increases fusion-related protein mitofusion2 (Mfn2) and decreases mitochondrial-associated dynamin-related protein 1 (Drp1), resulting in an increased number of elongated mitochondria and improved mitochondrial function. SIRT2 also attenuates the downregulation of transcription factor A, mitochondrial (TFAM), a key mitochondrial deoxyribonucleic acid (mtDNA)-associated protein, leading to an increase in mitochondrial mass. Glucose-6-phosphate dehydrogenase (G6PD) plays an important role in the oxidative stress response by producing nicotinamide adenine dinucleotide phosphate (NADPH) and the reduced form glutathione (GSH), which is associated with deacetylating G6PD and binding to nicotinamide adenine dinucleotide phosphate (NADP+). (C) Hypoxia-inducible factor1α (HIF1α), which is accumulated in the adipocytes of hypertrophy, represses SIRT2 expression, resulting in decreased deacetylation of PGC-1α and the expression of β-oxidation and mitochondrial genes. (Kitada, 2019).

Regulation of Mitochondrial Function: SIRT2 may be related to the regulation of mitochondrial function. Lemos et al. showed that SIRT2 is downregulated in insulin-resistant hepatocytes and the liver, and is accompanied by increased ROS production, activation of extracellular signal-regulated kinase (ERK1/2), and mitochondrial dysfunction in ob/ob mice. SIRT2 overexpression in insulin-resistant hepatocytes improved insulin sensitivity and reduced ROS production. SIRT2 might increase fusion-related protein mitofusion 2 (Mfn2) and decrease mitochondrial-associated dynamin-related protein 1 (Drp1), resulting in an increased number of elongated mitochondria and improving mitochondrial function. SIRT2 also attenuated the downregulation of transcription factor A mitochondrial (TFAM), a key mitochondrial deoxyribonucleic acid (mtDNA)-associated protein, leading to an increase in the mitochondrial mass. Furthermore, SIRT2 expression in peripheral blood mononuclear cells (PBMCs) from human subjects was negatively correlated with obesity, insulin resistance and oxidative stress. (Kitada, 2019).

SIRT2 is most markedly expressed in adipocytes. Nutrient overload-induced adipose expansion enhances intra-adipose hypoxia, promoting the accumulation of adipocyte hypoxia-inducible factor 1α (HIF1α). HIF1α suppresses SIRT2 transcription through interaction at a cross-species conserved hypoxic response element (HRE) on the SIRT2 promoter. HIF1α accumulation in the adipocytes of human obese subjects correlates with low levels of SIRT2 in visceral adipose tissue, and reduced SIRT2 activity directly translates into decreased deacetylation of PGC-1α and expression of β-oxidation and mitochondrial genes. HIF-1α suppresses fatty acid catabolism in mitochondria by negatively regulating the SIRT2-PGC-1α axis. (Kitada, 2019).

Heart Disease and Cardiovascular Disease

Heart failure is an aging-associated disease that is the leading cause of death worldwide. Sirtuin family members have been largely studied in the context of aging and aging-associated diseases. Heart failure is reversible by calorie restriction, a feeding regimen that limits calorie intake, or by physical exercise in animal models. Evidence suggests that health benefits of calorie restriction and exercise are mediated through the activation of NAD+-dependent class III histone deacetylases, called sirtuins. Of the seven different sirtuin isoforms (SIRT1 to 7), have been identified in mammals, SIRT2 has been shown to be highly expressed in the brain and the heart of humans. SIRT2 regulates nuclear envelope dynamics, cell metabolism, and autophagy. SIRT2 levels increase during calorie restriction and nutrient deprivation.

SIRT2 levels are known to be reduced in the visceral adipose tissue of human obese subjects, human liver tissues of iron overload, hepatocellular carcinoma samples, and cardiomyocytes from an animal model of type 1 diabetic mellitus. SIRT2-deficient mice show an increased incidence of mammary tumors and hepatocellular carcinoma. Similarly, SIRT2 deficiency increases susceptibility to colitis and iron deficiency-induced hepatocyte death.

Studies have also shown that SIRT2 deficiency promotes cardiac hypertrophy through impaired activation of AMP-activated protein kinase (AMPK)4 signaling in the heart. AMPK is the key regulator of cardiac energy homeostasis, and it regulates protein synthesis in heart during hypertrophy. (Sarikhani, Mohsen et al. "SIRT2 deacetylase represses NFAT transcription factor to maintain cardiac homeostasis." The Journal of biological chemistry vol. 293,14 (2018): 5281-5294. doi: 10.1074/jbc.RA117.000915). The decreased expression levels of SIRT2 cause the inactivation of AMP-activated protein kinases and promote cardiac hypertropy. It is essentially to correct the expression levels of SIRT2 in order to prevent and treat the disease. Left uncorrected, SIRT2 expression levels will remain ineffective to address the AMPK signaling and promote the progression of the disease.

Studies have identified the role of SIRT2 in regulating nuclear factor of activated T-cells (NFAT) transcription factor and the development of cardiac hypertrophy. While, SIRT2 is localized in the cytoplasm of cardiomyocytes, SIRT2 levels are reduced during pathological hypertrophy of the heart. Mouse studies show SIRT2-deficient mice develop spontaneous pathological cardiac hypertrophy, remodeling, fibrosis, and dysfunction in an age-dependent manner. Moreover, young SIRT2-deficient mice develop exacerbated agonist-induced hypertrophy. While the mechanism of SIRT2 in this manner is mediated by its function to bind to and deacetylates NFATc2 transcription factor, it is imperative to upregulate the expression levels of SIRT2 to maintain healthy function of the cardiac tissue. SIRT2 deficiency stabilizes NFATc2 and enhances nuclear localization of NFATc2, resulting in increased transcription activity. Inhibition of NFAT rescues the cardiac dysfunction in SIRT2-deficient mice. Ultimately, SIRT2 is a negative regulator of NFAT transcription factor. (Sarikhani, Mohsen et al. "SIRT2 deacetylase represses NFAT transcription factor to maintain cardiac homeostasis." The Journal of biological chemistry vol. 293,14 (2018): 5281-5294. doi: 10.1074/jbc.RA117.000915). By increasing SIRT2 expression and protein activity, nitroxide antioxidants such as Tempol promote negative regulation of NFAT to treat related heart diseases.

As with all other diseases, cardiovascular diseases can be defined by dysfunctional gene expression resulting in inappropriate protein activity. Heart failure is a growing public health problem and a leading cause of morbidity and mortality in modern society. Pathological cardiac hypertrophy induced by aging and neurohumoral activation (eg, angiotensin II [Ang II]) is an independent risk factor for heart failure.

Defects in myocardial metabolism are a major contributor to aging-related and stress-induced cardiac hypertrophy and subsequent heart failure. Aging and aging-related cardiac hypertrophy are regulated by several core metabolic sensors, including AMP-activated protein kinase (AMPK), SIRT1, mammalian target of rapamycin (mTOR), and IGF1R (insulin-like growth factor 1 receptor). For instance, AMPK is a major regulatory kinase that directly controls numerous metabolic processes, including fatty acid oxidation and glycolysis. AMPK can also regulate other metabolic pathways, such as the SIRT1, mTOR, and peroxisome proliferator-activated receptor gamma coactivator-1 alpha pathways. AMPK contains 1 catalytic subunit ($\alpha$) and 2 regulatory subunits ($\beta$ and $\gamma$). Mutations in the AMPK$\gamma$ subunit cause hypertrophic cardiomyopathy in humans. AMPK deficiency contributes to cardiac hypertrophy induced by aging, neurohumoral activation, pressure overload, and myocardial infarction. Activation of AMPK by AICAR (5-Aminoimidazole-4-carboxamide 1-$\beta$-D-ribofuranoside Acadesine N1-($\beta$-D-Ribofuranosyl)-5-aminoimidazole-4-carboxamide) or metformin protects the heart from cardiac hypertrophy induced by aging and other stresses. (SIRT2 Acts as a Cardioprotective Deacetylase in Pathological Cardiac Hypertrophy, Xiaoqiang Tang, Xiao-Feng Chen, Nan-Yu Wang, Xiao-Man Wang, Shu-Ting Liang, Wei Zheng, Yun-Biao Lu, Xiang Zhao, De-Long Hao, Zhu-Qin Zhang, Ming-Hui Zou, De-Pei Liu, and Hou-Zao Chen Originally published 25 Sep. 2017 2017; 136: 2051-2067).

SIRT2 promotes AMPK activation by deacetylating the kinase LKB1. Loss of SIRT2 reduces AMPK activation, promotes aging-related and Ang II-induced cardiac hypertrophy, and blunts metformin-mediated cardioprotective effects. (Xiaoqiang, 2017). This mechanism of SIRT2 is particularly important in an aged heart. Studies have found SIRT2 protein levels to be significantly downregulated in aged hearts compared with young hearts. The concentration of angiotension II (Ang II) is upregulated in aged hearts, and activation of the renin-angiotensin system is one of the core mechanisms underlying cardiac aging. Studies in mice have found that chronic infusion of Ang II recurs the development of cardiac hypertrophy observed in aged mice. Cardiac hypertrophy in young (8- to $\approx$12-week-old) mice was induced by subcutaneously infusing Ang II (1.3 mg/kg/d) into the mice for 4 weeks. Ang II infusion significantly increased circulating Ang II serum levels. SIRT2 protein levels were decreased in Ang II-induced hypertrophic hearts. As tubulin is a substrate of the deacetylase SIRT2. The level of acetylated Tubulin at lysine 40 was upregulated in aged and Ang II-induced hypertrophic hearts, indicating that SIRT2 activity was decreased in hypertrophic hearts. enzymatic activity of SIRT2 was also decreased in Ang II-induced hypertrophic hearts. (Xiaoqiang, 2017). Therefore, administration of a nitroxide corrects the downregulation of SIRT2 in an aged heart to promote healthy enzymatic activity and to inhibit Ang II cardiac hypertrophy. The disease is ultimately defined by the dysfunction in the gene expression of SIRT2. By correcting this dysfunction gene expression due to aging, and restoring SIRT2 activity in an aged heart, a nitroxide antioxidant, such as Tempol, can reverse the age-dependent conditions of the heart promoted by inhibition of SIRT2.

Diabetes and Insulin Resistance

The rising incidence of type 2 diabetes mellitus (T2DM) is a major public health concern, and novel therapeutic strategies to prevent T2DM are urgently needed worldwide. Aging is recognized as one of the risk factors for metabolic impairments, including insulin resistance and T2DM. Inflammation, oxidative stress, and mitochondrial dysfunction are closely related to both aging and metabolic disease. Calorie restriction (CR) can retard the aging process in organisms ranging from yeast to rodents and delay the onset of numerous age-related disorders, such as insulin resistance and diabetes. Among these sirtuins, SIRT1 and SIRT2 are located in the nucleus and cytoplasm, SIRT3 exists predominantly in mitochondria, and SIRT6 is located in the nucleus. These sirtuins regulate metabolism through their regulation of inflammation, oxidative stress and mitochondrial function via multiple mechanisms, resulting in the improvement of insulin resistance and T2DM. In this review, we describe the current understanding of the biological functions of sirtuins, especially SIRT1, SIRT2, SIRT3, and SIRT6, focusing on oxidative stress, inflammation, and mitochondrial function, which are closely associated with aging. (Kitada, 2019).

Chronic inflammation, oxidative stress and impaired mitochondrial function in skeletal muscle, adipose tissue or monocytes/macrophages are closely related to the pathogenesis of insulin resistance and T2DM. Additionally, inflammation and oxidative stress contribute to pancreatic $\beta$-cell dysfunction, contributing to the progression of T2DM. (Id.).

The activation of monocytes in the circulation, adipocytes and macrophages residing in adipose tissue leads to the release of various inflammatory mediators, including tumor necrosis factor-$\alpha$ (TNF-$\alpha$), interleukin-6 (IL-6), and chemoattractant protein-1 (MCP-1), in insulin-resistant and diabetic states. These cytokines activate inflammatory signaling pathways, such as the inhibitor of I$\kappa$B kinase (IKK) and c-Jun NH2-terminal kinase (JNK) pathways, which impair the insulin signaling pathway by modulating phosphoinositide 3-kinase (PI3K) and Akt, and they play a crucial role in the pathogenesis of insulin resistance in adipose tissue and skeletal muscle. Oxidative stress also impairs insulin signaling, which contributes to insulin resistance in T2DM. In insulin-resistant or diabetic states, in addition to hyperglycemia, other metabolites, including free fatty acids (FFAs) and certain cytokines, such as TNF-$\alpha$, induce the overproduction of ROS from mitochondria. ROS trigger the activation of serine/threonine kinases, such as p38 mitogen-activated protein kinase (p38 MAPK), JNK, and IKK, which induce the serine phosphorylation of insulin receptor substrate-1 (IRS-1), and then degrade IRS-1 and reduce IRS-1 tyrosine phosphorylation, leading to the suppression of insulin signaling, as well as inflammation. Inflammatory mediators and oxidative stress are also related to pancreatic $\beta$-cell dysfunction, resulting in the impairment of insulin production or excretion from $\beta$ cells. (Kitada, 2019).

SIRT2 is unique in that it is the only sirtuin known to exist in both the mitochondria and cytosol. Like all members of the sirtuin family, SIRT2 is NAD+-dependent. SIRT2 links lysine acetylation to cellular energy homeostasis, as this reaction is regulated by both acetyl-CoA availability and NAD+ levels. In accordance with this, protein acetylation is determined by nutritional and metabolic states Overnutrition and obesity lead to increased lysine acetylation as a consequence of increased acetyl-CoA. This form of protein hyperacetylation contributes to the pathogenesis of insulin resistance and type 2 diabetes. (Lantier, Louise et al. "SIRT2 knockout exacerbates insulin resistance in high fat-fed mice." PloS one vol. 13,12 e0208634. 11 Dec. 2018, doi: 10.1371/journal.pone.0208634).

Studies have shown the link between glucose homeostasis and mitochondrial protein acetylation, providing support that these events are coupled. The link between increased mitochondrial protein acetylation and impaired glucose metabolism is particularly alarming. During overnutrition, as various models of muscle mitochondrial hyperacetylation show impaired glucose metabolism. Studies have evaluated the genetic and dietary means effect of increased acetylation state. Mice with a whole-body knockout of SIRT2 and their wildtype littermates were fed a chow or high fat diet. Loss of SIRT2 induce hyperacetylation and impaired insulin sensitivity. It was shown that insulin resistance due to diet-induce obesity would be exacerbated with deletion of the SIRT2 gene. (Lantier, 2018). Given that the loss of SIRT2 confers insulin resistance due to mitochondrial hyperacetylation, increasing SIRT2 expression to increase protein concentration and activity prevents insulin resistance and regulates glucose metabolism.

Cancer

One of the fundamental observations in oncology is that tumorigenesis increases as a function of age and in fact, increasing age is the strongest statistic variable that predicts for carcinogenesis. Furthermore, aging is a complex cellular process that appears to be regulated, at least in part, by several signaling protein families that have been identified in multiple species. One of the most influential functions of the siturin gene family is the regulation of critical signaling networks, and following stress, several mice lacking one of the sirtuin genes develop illnesses that mimic those observed in older humans. This observation suggests that the cellular and molecular processes and mechanisms that direct an organism's life span may be used to determine the clinical connection between aging and carcinogenesis. Studies have shown that Sirt2 is a legitimate tumor suppressor protein. Mice genetically altered to delete Sirt2 develop gender-specific tumorigenesis, with females primarily developing mammary tumors, and males developing multiple different types of gastrointestinal malignancies. Furthermore human tumors, as compared to normal samples, displayed significant decreases in SIRT2 levels showing that SIRT2 is a human tumor suppressor. (Park, S., Zhu, Y., Ozden, O., Kim, H., Jiang, H., Deng, C., Gius, D., & Vassilopoulos, A. (2012). SIRT2 is a tumor suppressor that connects aging, acetylome, cell cycle signaling, and carcinogenesis. Translational Cancer Research, 1(1), 15-21. doi: 10.21037/370)

Decreased expression and inhibited activity of SIRT2 has been shown to promote the progression and development of several different cancer types. SIRT2 functions as a tumor suppressor based on evidence that SIRT2 mRNA and protein levels are lower in glioma, gastric cancer and melanoma compared with normal tissues, and forced expression of SIRT2 inhibits cancer cell proliferation and colony formation in non-small cell lung cancer.

Ovarian cancer is one of the most common cancers that affects women. Ovarian cancer has the third highest incidence of gynecological oncology, with the incidences of only cervical and uterine cancer being higher amongst women. Ovarian epithelial cancer is the most common type of cancer affecting the ovaries and the most lethal of all gynecologic malignancies. SIRT2 is important in the prevention of ovarian cancer metastasis. Statistical analysis did not indicate that low expression of SIRT2 was associated with increased lymph node metastasis, as peritoneal dissemination and local direct spread are the two main methods of ovarian cancer metastasis. SIRT2. Part of the mechanism of SIRT2 tumor suppression is due to the interaction between SIRT2 and CDK4. Studies have shown upregulation of CDK4 expression and nuclear accumulation of CDK4 in malignant ovarian cancers, and CDK4-induced cell proliferation. In addition to ovarian cancer, elevated expression of CDK4 has also been observed in other malignancies. By increasing SIRT2, CDK4 activity is inhibited in the progression and development of CDK4 mediated carcinogenesis.

In gliomas and melanomas, SIRT2 plays several different roles from mitotic checkpoint regulation to cellular metabolism. Studies have shown SIRT2 protein and RNA levels are decreased in gliomas, melanomas, and gastric carcinomas (Hiratsuka et al., 2003). Furthermore, in human gliomas SIRT2 inhibits colony formation (Hiratsuka et al., 2003). In melanomas SIRT2 is mutated in the catalytic domain, eliminating its enzymatic activity (Lennerz et al., 2005). Another important observation is that when the SIRT2 mutant (phosphorylation site) is overexpressed in a glioblastoma cell line, it leads to a reduction of hyperploid cells under mitotic stress exposure (North and Verdin, 2007). The enzymatic activity of SIRT2 is crucial for the prevention and inhibition of carcinogenesis regarding gliomas, melanomas, and gastric cancers. Where SIRT2 is decreased or inhibited, administration of a nitroxide antioxidant supports the healthy enzymatic activity of SIRT2 to prevent and treat the underlying dysfunction gene expression resulting in the treatment and prevention of cancer development. (de Oliveira, Rita Machado et al. "SIRT2 as a Therapeutic Target for Age-Related Disorders." Frontiers in pharmacology vol. 3 82.3 May. 2012, doi: 10.3389/fphar.2012.00082).

SIRT2 expression is decreased in human gliomas, and ectopic expression of SIRT2 in glioma cell lines led to a reduction of in vitro colony formation ability. In addition, it has been suggested that loss of SIRT2 promotes genomic instability that is a well established early event in carcinogenesis. (Park, 2012). The research shows that a decrease in SIRT2 promotes cancer formation and growth through inhibited protein activity. In cancer where SIRT2 gene is underexpressed, the prognosis and progression will favor carcinogenesis and tumorgenesis. By treating the SIRT2 gene to increase expression levels and increase the encoded proteins, nitroxide antioxidants, such as Tempol, treat the disease of cancer by upregulating the expression of SIRT2 in disease promoted by a decreased or underexpression of SIRT2.

Neurodegenerative Diseases and Neurological Disorders

Studies suggest SIRT2 is the most highly expressed in brain tissue, particularly in the cortex, striatum, spinal cord, and postnatal hippocampus, indicating that SIRT2 is involved in neural development. Studies show that SIRT2 is crucial for myelination whether in the central nervous system (CNS) or peripheral nervous system. In the CNS, SIRT2 is mainly expressed in oligodendrocytes (OLs) and is considerably upregulated during OL differentiation and myelination. In the peripheral nervous system, SIRT2 ablation in mouse Schwann cells (SCs) delayed myelin formation and postinjury remyelination. Moreover, SIRT2 is involved in other developmental processes in the nervous system as SIRT2 gene knockout mice demonstrated dysfunctions of the nervous system, such as defects in differentiation of dopaminergic (DA) neurons, aberrant synaptic plasticity with impaired learning and memory, and morphological changes of mitochondria in the cortex. (Zhang, Lin et al. "The Clinical Significance of SIRT2 in Malignancies: A Tumor Suppressor or an Oncogene?." Frontiers in oncology vol. 10 1721. 8 Sep. 2020, doi: 10.3389/fonc.2020.01721). Increasing the expression level of SIRT2 in neuronal tissue promotes healthy neuron tissue development and prevents associated diseases with demyelintation.

In addition to act as a crucial regulator in neurodevelopment, SIRT2 is also associated with nervous system disorders, in particular, neurodegenerative diseases [Parkinson's disease (PD), Alzheimer's disease (AD), and Huntington's disease (HD). SIRT2 expression participates in the aggregation process of proteins such as α-synuclein (α-syn), huntingtin, as well as amyloid-β peptide (Aβ), and hyperphosphorylated tau protein, involved in PD, HD, and AD, respectively. Mounting evidence showed that inhibition of SIRT2 function, either pharmacologically or genetically, provided neuroprotection in a variety of mice modals, suggesting that SIRT2 could be a potential therapeutic target for these diseases. (Zhang, 2020).

Decreased SIRT2 expression has also been found to cause several neurological disorders such as depression, and bipolar disorder. SIRT2 mRNA is decreased in the peripheral white blood cells of patients with major depressive disorder (MDD) or bipolar disorder (BPD), and SIRT2 overexpression in the hippocampus of mice promotes neurogenesis and reverses chronic unpredictable stress (CUS)-induced depressive-like behaviors. (Wang, Sung Eun et al. "Downregulation of SIRT2 by Chronic Stress Reduces Expression of Synaptic Plasticity-related Genes through the Upregulation of Ehmt2." Experimental neurobiology vol. 28, 4 (2019): 537-546. doi: 10.5607/en.2019.28.4.537).

Susceptibility or resilience to stress appears to be regulated by epigenetic mechanisms including histone modification. Class I and II HDACs are involved in the behavioral response to chronic stress and antidepressants in rodents, suggesting the possibility of using HDAC inhibitors in patients with treatment-resistant depression. Methylation of histones is an additional epigenetic mechanism involved in depression. Chronic stress induces the expression of euchromatic histone-lysine N-methyltransferase 2 (Ehmt2) involved in complexes repressing transcription. Ehmt2-induced di-methylated histone 3 lysine 9 (H3K9me2) is a marker of repression induced in the hippocampus and amygdala during stress and anxiety (Wang, 2019).

Studies have shown that chronic stress-induced downregulation of SIRT2 increases expression of histone methyltransferases in the hippocampus of a mouse depression model, resulting in transcriptional repression of synaptic plasticity-related genes. Furthermore, knockdown of SIRT2 in the dentate gyms (DG) precipitated depression-like behaviors in mice, accompanied by reduced expression of synaptic plasticity-related genes. (Wang, 2019). Administration of a nitroxide antioxidant, such as Tempol, increases expression levels of SIRT2 to restore, treat, and reverse the dysfunctional expression causing these neurological disorders. By correcting the dysfunction in the gene expression, the manifestation of the inhibited protein activity is treated.

Aging and Age-Related Disease

Sirtuin proteins are conserved regulators of aging that have recently emerged as important modifiers of several diseases which commonly occur later in life such as cancer, diabetes, cardiovascular, and neurodegenerative diseases.

Mechanistically, SIRT2 deacetylates lysine residues in the catalytic domain of p300, a histone acetyltransferase, which maintains its active form by autoacetylation (Black et al., 2008). The known consequence of SIRT2-dependent deacetylation of p300 is the de-repression of p53 transcriptional activity. (de Oliveira, Rita Machado et al. "SIRT2 as a Therapeutic Target for Age-Related Disorders." Frontiers in pharmacology vol. 3 82. 3 May. 2012, doi: 10.3389/fphar.2012.00082).

When considering age-related diseases, studies have shown several diseases with increased incidence that correlates with increased age. For example, metabolic syndrome In western societies high fat and low fiber diets, together with a sedentary life style, are associated with a high prevalence of metabolic syndrome, that increases with age (Ford et al., 2002). Metabolic syndrome is the condition brought about by: obesity; insulin resistance; hypertension; and elevated lipid content in the blood. Metabolic syndrome increases the risk of serious health problems (Moller and Kaufman, 2005). In the obese it is the proportion of body fat which is significant, not purely weight per se. Dramatically, obesity is associated with a decrease in life expectancy (Haslam and James, 2005). Looking specifically to SIRT2 function in adipocytes, SIRT2 decreases during preadipocyte differentiation and regulates adipocyte differentiation in a negative manner by deacetylating FOXO1. Deacetlyation of FOXO1 by SIRT2 can reduce the total concentration of adipocytes and adipose tissue. (Id).

SIRT2 further regulates glucose equilibrium and metabolism by stabilizing and interacting with phosphoenolpyruvate carboxykinase 1. By deacetylating and stabilizing phosphoenolpyruvate carboxykinase 1 (PEPCK1), an important enzyme in gluconeogenesis (Jiang et al., 2011). When SIRT2 is activated by low glucose conditions, PEPCK1 is stabilized and it shifts the equilibrium toward the generation of glucose from non-carbohydrate carbon sources, mimicking a fast or exercise state in the organisms. Conversely, in the presence of high glucose SIRT2 expression is suppressed, leading to PEPCK1 degradation by the ubiquitin proteasome system. Where a subject is found to have destabilized or unregulated PEPCK1 activity, upregulation of SIRT2 promotes healthy cellular function relating to glucose metabolism through regulation of PEPCK1. Treatment with a nitroxide to increase expression levels of SIRT2 prevents and treats the diseases associated with dysfunctional glucose metabolism by addressing the underlying cause of the disease and correcting the regulatory capacity of SIRT2 through adjusting the expression level to an increased and healthy state.

Methods for Treating Genetic Diseases Associated with Decreased SIRT2 Activity

Some embodiments disclosed herein provide methods for treating genetic diseases associated with decreased SIRT2 activity in a human subject in need thereof, comprising (optionally) identifying a human subject having a genetic disease and in need of an increased expression level of a SIRT2 gene; and administering to the human subject an effective amount of a nitroxide antioxidant. In some embodiments, the methods disclosed herein are be used to treat a human subject that shows no symptoms of the genetic disease, but is at risk of having the genetic disease. Exemplary risk factors for genetic diseases include, but are not limited to, age, family history, health conditions, medical history, habits, or a combination thereof. In some embodiments, risk factors for genetic disease comprise a decreased expression level of SIRT2.

In some embodiments, administering to the human subject an effective amount of the nitroxide antioxidant results in an increased expression level of a gene, for example SIRT2. The genes associated with sirtuin proteins can be SIRT1, SIRT2, SIRT3, SIRT4, SIRT5, SIRT6, SIRT7, or a homologue thereof. The treatment of the human subject with the effective amount of the nitroxide antioxidant results in an increased expression level of the gene. For example, the treatment results in an increased expression level of SIRT2. The increased expression level of SIRT2, increases the quantity of the encoded protein and improve mitochondrial function inhibited by decreased expression levels. The improved and corrected sirtuin activity and mitochondrial function reduces, prevents, or eliminates the signs and symptoms of a genetic disease associated with decreased SIRT2 function, including the curing of the genetic disease.

In some embodiments, the levels of SIRT2 in the connective tissue, muscle tissue, nervous tissue, and/or epithelial tissue may change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Non-limiting examples of genetic diseases associated with decreased SIRT2 activity include Osteogenesis imperfecta, Spondyloepiphyseal dysplasia, Spondyloepimetaphyseal dysplasia, Achondrogenesis, hypochondrogenesis, Kniest dysplasia, Stickler syndrome, Ehlers-Danlos syndrome, Familial porencephaly, Hereditary angiopathy with nephropathy, aneurysms and muscle cramps syndrome, Benign familial haematuria, Alport syndrome, Leiomyomatosis, Bethlem myopathy, Ullrich congenital muscular dystrophy, Dystrophic epidermolysis bullosa, Corneal endothelial dystrophies Multiple epiphyseal dysplasia, Autosomal recessive Stickler syndrome, Schmid metaphyseal chondrodysplasia, Marshall syndrome, Otospondylomegaepiphyseal dysplasia Deafness, Junctional epidermolysis bullosa-other Knobloch syndrome.

Methods for Counteracting Treating a Disease Related to Aging

Some embodiments disclosed herein provide methods for counteracting age-related increase in gene expression or treating an age-related disease, comprising (optionally) identifying a human subject over the age of 35 and having a decreased expression level of SIRT2 or an age-related disease; and administering to the human subject an effective amount of a nitroxide antioxidant. In some embodiments, the methods comprise determining the expression level of SIRT2. The identification step and/or the determination step may not be necessary in some instances, such as where a decreased expression level of SIRT2 is inferred from the human subject's age, family history, health conditions, medical history, habits, or a combination thereof. In some embodiments, the methods disclosed herein are used to treat a human subject shows no symptoms of an age-related disease, but is at risk of having an age-related disease. Exemplary risk factors for an age-related disease include, but are not limited to, age, family history, health conditions, medical history, habits, or a combination thereof. In some embodiments, risk factors for an age-related disease comprise a decreased expression level of SIRT2.

In some embodiments, administering to the human subject an effective amount of the nitroxide antioxidant results in an increased expression level of a gene, for example SIRT2. The genes associated with sirtuin proteins can be SIRT1, SIRT2, SIRT3, SIRT4, SIRT5, SIRT6, SIRT7, or a homologue thereof. The treatment of the human subject with the effective amount of the nitroxide antioxidant results in a increased expression level of the gene. For example, the treatment results in an increased expression level of SIRT2. The increased expression level of SIRT2, corrects mitochondrial function and sirtuin activity to a healthy level within the cell. The corrected level of sirtuin activity and mitochondrial function results in a decrease in or disappearance of signs and symptoms of an age-related disease associated with decreased SIRT2 function, including the curing of the age-related disease.

In some embodiments, the levels of SIRT2 in the connective tissue, muscle tissue, nervous tissue, and/or epithelial tissue may change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Some embodiments disclosed herein provide methods for treating a disease related to aging in a human subject in need thereof, comprising (optionally) identifying a human subject over the age of 35 and having an age-related disease and having a decreased expression level of the SIRT2 gene; and administering to the human subject an effective amount of a nitroxide antioxidant. Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with sirtuin 2 is increased.

Non-limiting examples of age-related diseases include cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension.

Methods for Increasing Expression Level of a Gene

Some embodiments disclosed herein provide methods for increasing the expression level of a gene in a human subject in need thereof, comprising (optionally) identifying a human subject having a decreased expression level of a SIRT2 gene; and administering to the human subject an effective amount of a nitroxide antioxidant. Some embodiments disclosed herein provide methods for treating a disease associated with decreased SIRT2 activity in a patient in need thereof, comprising (optionally) identifying a human subject having a decreased expression level of SIRT2; and administering to the human subject an effective amount of a nitroxide antioxidant. The increased expression level may be age-related, or disease related. In some embodiments, the disease may be cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension, or any combination thereof. Some embodiments disclosed herein provide methods for treating an individual in need thereof, comprising (optionally) identifying a human subject over the age of 35 in need of an increased expression level of a SIRT2 gene; and administering to the human subject an effective amount of a nitroxide antioxidant. In some embodiments, the methods comprise determining the expression level of SIRT2. In some embodiments, the determination step comprises inferring decreased expression level of SIRT2 based on the human subject's age, family history, health conditions, medical history, habits, or a combination thereof. In some embodiments, the methods disclosed herein are used to treat a human subject shows no symptoms of a disease associated with decreased SIRT2 function, but is at risk of having a disease associated with decreased SIRT2 function. Exemplary risk factors for a disease associated with decreased SIRT2 function include, but are not limited to, age, family history, health conditions, medical history, habits, or a combination thereof.

In some embodiments, administering to the human subject an effective amount of the nitroxide antioxidant results in an increased expression level of a gene, for example a gene associated with sirtuin protein activity. The gene associated with sirtuin 2 can be SIRT2, SIRT1, SIRT3, SIRT4, SIRT5, SIRT6, SIRT7. The treatment of the human subject with the effective amount of the nitroxide antioxidant results in an increased expression level of the gene. For example, the treatment can decrease the expression levels of SIRT2. The increased expression of the gene counteracts the decrease in the expression level of the gene.

Methods for Treating Cancer

Some embodiments disclosed herein provide methods for treating cancer in a human subject in need thereof, comprising (optionally) identifying a human subject having a cancer and in need of an increased expression level of a SIRT2 gene; and administering to the human subject an effective amount of a nitroxide antioxidant. In some embodiments, the methods disclosed herein are used to treat a human subject that shows no symptoms of cancer, but is at risk of having cancer. Exemplary risk factors for cancer include, but are not limited to, age, family history, health conditions, medical history, habits, or a combination thereof. In some embodiments, risk factors for cancer comprise a decreased expression level of SIRT2.

Non-limiting examples of the methods for identifying a human subject having a cancer include colonoscopy; sigmoidoscopy; and high-sensitivity fecal occult blood tests. In some embodiments, methods for identifying a human subject having a cancer include low-dose helical computed tomography; mammography; and pap test and human papillomavirus (HPV) testing. In some embodiments, methods for identifying a human subject having a cancer include alpha-fetoprotein blood test; breast magnetic resonance imaging (MRI); CA-125 test; clinical breast exams and regular breast self-exams; prostate-specific antigen (PSA) testing; skin exams; transvaginal ultrasound; and virtual colonoscopy. In some embodiments, methods for identifying a human subject having a cancer include barium enema; biopsy; bone marrow aspiration and biopsy; bone scan; breast MRI for early detection of breast cancer; breast MRI; colonoscopy; computed tomography (CT) scan; digital rectal exam (DRE); blood and platelets testing; bone marrow testing; umbilical cord blood testing; electrocardiogram (EKG) and echocardiogram; endoscopic techniques; fecal occult blood tests; magnetic resonance imaging (MRI); mammography; multi gated acquisition (MUGA) scan; papanicolaou (pap) test; positron emission tomography and computed tomography (PET-CT) scan; sigmoidoscopy; tumor marker tests; ultrasound; upper endoscopy. In some embodiments, methods for identifying a human subject having a cancer include DNA sequencing; detecting presence of single nucleotide polymorphism (SNIP); and detecting the presence of certain protein markers.

In some embodiments, administering to the human subject an effective amount of the nitroxide antioxidant results in an increased expression level of a gene, for example a gene associated with sirtuin protein activity. The gene associated with sirtuin activity can be SIRT1, SIRT2, SIRT3, SIRT4, SIRT5, SIRT6, SIRT7. The treatment of the human subject with the effective amount of the nitroxide antioxidant results in an increased expression of the gene. For example, the treatment results in an increased expression level of SIRT2. The increased expression level of the gene can modulate mitochondrial function and sirtuin activity to a healthy rate and function. The improved mitochondrial function and sirtuin activity results in a decrease in or disappearance of signs and symptoms of the cancer, including the curing of the cancer.

Non-limiting examples of cancer include bladder and other urothelial cancers; breast cancer; cervical cancer; colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non-hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyPerproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumors, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood; ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Methods for Treating Autoimmune Diseases

Some embodiments disclosed herein provide methods for treating an autoimmune disease in a human subject in need thereof, comprising (optionally) identifying a human subject having an autoimmune disease and in need of an increased expression level of a SIRT2 gene; and administering to the human subject an effective amount of a nitroxide antioxidant. In some embodiments, the methods disclosed herein are used to treat a human subject shows no symptoms of an autoimmune disease, but is at risk of having an autoimmune disease. Exemplary risk factors for an autoimmune disease include, but are not limited to, age, family history, health conditions, medical history, habits, or a combination thereof. In some embodiments, risk factors for an autoimmune disease comprise a decreased expression level of SIRT2.

In some embodiments, Autoimmunity is the system of immune responses of an organism against its own healthy cells and tissues. Any disease that results from such an aberrant immune response is termed an "autoimmune disease". Prominent examples include celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM). Autoimmune diseases are very often treated with steroids In some embodiments, administering to the human subject an effective amount of the nitroxide antioxidant results in an increased expression level of a gene, for example a gene associated with sirtuin protein activity. The gene associated with sirtuin proteins can be SIRT1, SIRT2, SIRT3, SIRT4, SIRT5, SIRT6, SIRT7. The treatment of the human subject with the effective amount of the nitroxide antioxidant results in an increased expression level of the gene. For example, the treatment results in an increased expression level of SIRT2. The increased expression levels of SIRT2, increases mitochondrial function and sirtuin activity resulting in a decrease in or disappearance of signs and symptoms of the autoimmune disease, including the curing of the autoimmune disease. In some embodiments, the increased expression level of SIRT2, improves mitochondrial function. The improved mitochondrial function results in a decrease in or disappearance of signs and symptoms of the autoimmune disease, including the curing of the autoimmune disease.

Non-limiting examples of autoimmune diseases include rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GB S) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

Non-limiting examples of autoimmune diseases include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidymitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjögren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

Nitroxide Antioxidant

Nitroxide antioxidants describes a group of stable organic molecules, containing the nitroxyl group >N—O· with an unpaired electron. They have a low molecular weight, are non-toxic, do not elicit immunogenic effects on cells and easily diffuse through cell membranes. Their biological activity as antioxidants is related to the regulation of redox state in the cells. Nitroxides can undergo cyclic oxidation or reduction reactions. Their antioxidant activity is related to several mechanisms such as the direct scavenging of free radicals, transition metal ion oxidation. In addition, nitroxides exhibit superoxide dismutase (SOD)-like activity, modulate its catalase-like activity and ferroxidase-like activity, and are the inhibitors of free radical reactions such as lipid peroxidation. Nitroxides have dynamic beneficial impact on all cellular processes from inhibition of oxidative stress and reducing inflammation, while under certain conditions they may also lead to its intensification, for example, in tumor cells. The different beneficial impact on cellular processes provides each cell with necessary support to prevent or reverse diseases and conditions through optimizing cellular activity and associated biological processes in a healthy state and promoting cell death in diseases such as cancer.

Cyclic nitroxides, also known as aminoxyls or nitroxyls, are stable free radicals stabilized by methyl groups at the a position in five-membered pyrrolidine, pyrroline or oxazolidine and six-membered piperidine ring structures. The methyl groups confer stability to the nitroxide radicals by preventing radical-radical dismutation and also limit access to reactive substances, which can quench the radical species. The substituent groups on the ring (denoted by R-) produce a diverse range of compounds that can be directed to specific hydrophilic or hydrophobic regions in the cellular microenvironment. The redox transformations between the oxidation states of nitroxide, hydroxylamine and the oxoammonium cation acts as an efficient redox couple, which can support catalytic processes via reversible electron redox reactions.

(Soule, Benjamin P et al. "The chemistry and biology of nitroxide compounds." Free radical biology & medicine vol. 42,11 (2007): 1632-50. doi: 10.1016/j.freeradbiomed.2007.02.030).

The mechanism of action exerted by nitroxide antioxidants is very unique. In particular, nitroxide antioxidant function is characterized by a catalytic mechanism of action associated with a single-electron redox cycle. Their reduction results in the generation of hydroxylamine and oxidation in oxoammonium ion; meanwhile both reactions are reversible and repetitive such that the ratio of free radicals suppressed by nitroxide antioxidants is significantly higher than natural antioxidant processes within a cell. Hydroxylamine also exhibits antioxidant properties because it is easily oxidized to nitroxide. As mentioned above, the nitroxides devoid of electrical charge easily diffuse through the cell membranes, thus they can also inactivate the reactive oxygen species formed in the cells and modulate the concentration of intracellular nitric oxide. Their molecular structure and composition make nitroxide antioxidants additionally efficacious in tissues that prevent transport of different molecules, such as neuronal tissue across the blood brain barrier.

Non-limiting examples of the nitroxide antioxidant include 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Amin omethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, 2,2,6,6-tetramethyl-4-oxo-1-piperidinyloxy (TEMPONE), 1-Hydroxy-2,2,6,6-tetramethyl-4-oxo-piperidine. HCl (TEMPONE-H), 1,2-dipalmitoyl-sn-glycero-3-phospho(tempo)choline (TEMPO PC), (4-[N,N-dimethyl-N-(2-hydroxyethyl)]ammonium-2,2,6,6-tetramethylpiperidine-1-oxyl (TEMPO Choline), and the like.

The use of other nitroxide compounds is also contemplated. Nitroxide stable radicals demonstrate effective antioxidative activity in various biological systems ranging from molecular, cellular, and laboratory animal level. Nitroxides have been reported to catalyze O2. dismutation through two different catalytic pathways including reductive and oxidative reaction mechanisms. Conversely, kinetics analysis of rapid mixing stopped flow experiments de-signed to measure the effect of nitroxides on superoxide decay did not reveal any SOD activity, leading to the conclusion that nitroxides act as free radical scavengers.

Studies have shown that unlike other antioxidants, nitroxides are characterized by a catalytic mechanism of action associated with a single-electron redox cycle. Their reduction results in the generation of hydroxylamine and oxidation in oxoammonium ion; meanwhile both reactions are reversible. Hydroxylamine also exhibits antioxidant properties because it is easily oxidized to nitroxide. Nitroxide antioxidants undergo redox cycles. They are easily reduced to hydroxylamines and oxidized to oxoammonium salts.

According to certain embodiments the nitroxide compound can be selected from the following formulas:

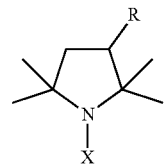

wherein X is selected from O— and OH, and R is selected from COOH, CONH, CN, and CH2NH2;

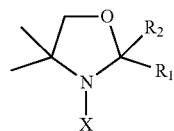

wherein X is selected from O— and OH, and R1 is selected from CH3 and spirocyclohexyl, and R2 is selected from C2H5 and spirocyclohexyl;

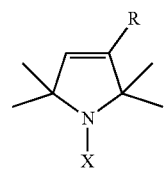

wherein X is selected from O— and OH and R is selected from CONH; and

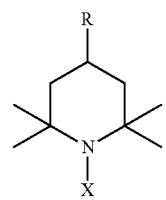

wherein X is selected from O— and OH and R is selected from H, OH, and NH2.

Suitable nitroxide compounds can also be found in Proctor, U.S. Pat. No. 5,352,442, and Mitchell et al., U.S. Pat. No. 5,462,946, both of which are hereby incorporated by reference in their entireties.

In some embodiments, the nitroxide antioxidant has a general formula:

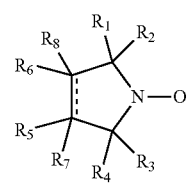

wherein the dashed line denotes a saturated bond or an unsaturated bond, wherein when the dashed line denotes an unsaturated bond, R7 and R8 are absent; R1-R4 are each independently a C1-4-alkyl, or alternatively, R1 and R2, and/or R3 and R4, together form a 3-7-membered alicyclic ring; and R5-R8 are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino.

In some embodiments, the nitroxide antioxidant includes or is associated with (e.g., binds to or is conjugated with) a bioeffector molecule. For example, the bioeffector molecule is a targeting subunit bound to the nitroxide antioxidant, such as a mitochondrial targeting subunit. A targeting subunit can direct activity of the nitroxide antioxidant to a predetermined location within or on the cell. Non-limiting examples of mitochondrial targeting bioeffector molecules includes triphenylphosphine (TPP), gramicidin, and any functional group effectively charged to be attracted to the polarized mitochondria.

In some embodiments, the nitroxide antioxidant is structurally cyclic having a ring structure including a nitroxide molecule incorporated therein. In some embodiments, the nitroxide antioxidant is characterized as the nitroxide molecule functioning as the catalytic center.

Dosage

In some embodiments, the nitroxide antioxidant, nontoxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 4000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g. glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nixtroxide antioxidant and are administered by methods known in the art.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

EXAMPLES

Some aspects of the embodiments discussed above are disclosed in further detail in the following examples, which are not in any way intended to limit the scope of the present disclosure.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1. Effects of Tempol on Expression of Genes Associated With Sirtuin Protein Activity To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that SIRT2 exhibited statistically significant increase in expression. This result is shown in Table 1.

TABLE 1

Genes Associated With SIRT2 Exhibiting Increased Expression In Cardiac Tissue After Tempol Administration

| Symbol | Gene title | Fold change | P-value |
| --- | --- | --- | --- |
| SIRT2 | Sirtuin 2 | 1.16 | 0.00 |

Example 2. Treating Age-Related Increase in Gene Expression

A 70-kilogram human subject over the age of 65 is identified as having, or known to have, or suspected of having a decreased expression level of SIRT2. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

Example 3. Treating a Human Subject with Increased Gene Expression

A 70-kilogram human subject is identified as having, or known to have, or suspected of having a decreased expression level of SIRT2. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

Example 4. Treating a Human Subject with an Age-Related Disease

A 70-kilogram human subject over the age of 65 and having a cardiovascular disease is identified for a decreased expression level of SIRT2. Or a 70-kilogram human subject over the age of 65 is known to have a cardiovascular disease and/or decreased expression level of SIRT2. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

Example 5. Treating a Human Subject at Risk of Developing Cancer

A 70-kilogram human subject at risk of developing colorectal cancer is identified for decreased expression level of SIRT2. Or a 70-kilogram human subject is known to be at risk of developing colorectal cancer and/or have decreased expression level of SIRT2. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

Example 6. Treating a Human Subject at Risk of Developing an Autoimmune Disease A 70-kilogram human subject at risk of developing an autoimmune disease (e.g., rheumatoid arthritis) is identified for decreased expression level of SIRT2. Or a 70-kilogram human subject is known to be at risk of developing an autoimmune disease and/or have decreased expression level of SIRT2. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

Example 7. Treating a Human Subject at Risk of Developing a Condition Due to Aging A 70-kilogram human subject of 45 years old at risk of developing a condition due to aging is identified. Or a 70-kilogram human subject of 45 years old is known to be at risk of developing a condition. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

Example 8. Treating a Human Subject at Risk of Developing a Neruodegenerative Disease A 70-kilogram human subject at risk of developing a neurodegenerative disease (e.g., Parkinson's Disease) is identified for decreased expression level of SIRT2. Or a 70-kilogram human subject is known to be at risk of developing a neurodegenerative disease and/or have decreased expression level of SIRT2. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

Example 9. Treating a Human Subject Having an Infection

A 70-kilogram human subject having an infection (e.g., a bacterial, fungal, or viral infection) is identified for decreased expression level of SIRT2. Or a 70-kilogram human subject is known to have an infection and/or have decreased expression level of SIRT2. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of SIRT2, is increased.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of increasing expression level of a gene encoding SIRT2 in a human subject, the method comprising:
   identifying a human subject having both a decreased expression level of a gene encoding SIRT2 compared to a population of individuals of the same sex and similar age, and a disease or condition associated with decreased expression level of the gene encoding SIRT2, wherein the disease or condition is selected from the group consisting of systemic lupus erythematosus (SLE), cataracts, and osteoporosis; and
   administering an effective amount of a nitroxide antioxidant to the subject, the nitroxide antioxidant selected from the group consisting of 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Aminomethyl-PROXYL, 3-Cyano-PROXYL, 3-Carbamoyl-PROXYL, 3-Carboxy-PROXYL, 4-Oxo-TEMPO, 2,2,6,6-tetramethyl-4-oxo-1-piperidinyloxy (TEMPONE), 1-Hydroxy-2,2,6,6-tetramethyl-4-oxo-piperidine HCl (TEMPONE-H), 1,2-dipalmitoyl-sn-glycero-3-phospho (tempo) choline (TEMPO PC), and (4-[N,N-dimethyl-N-(2-hydroxyethyl)]ammonium-2,2,6,6-tetramethylpiperidine-1-oxyl (TEMPO Choline),
   whereby the administration of the nitroxide antioxidant increases the expression level of the gene encoding SIRT2.

2. The method of claim 1, wherein the nitroxide antioxidant is TEMPOL.

3. The method of claim 1, wherein the nitroxide antioxidant is OXANO.

4. The method of claim 1, wherein the nitroxide antioxidant is TEMPO.

5. The method of claim 1, wherein the nitroxide antioxidant is Tempamine.

6. The method of claim 1, wherein the nitroxide antioxidant is TEMPONE.

7. The method of claim 1, wherein the nitroxide antioxidant is TEMPONE-H.

8. The method of claim 1, wherein the nitroxide antioxidant is TEMPO PC.

9. The method of claim 1, wherein the nitroxide antioxidant is 3-Carboxy-PROXYL.

10. The method of claim 1, wherein the nitroxide antioxidant is TEMPO Choline.

11. The method of claim 1, wherein identifying a human subject having a decreased expression level of a gene encoding SIRT2 compared to a population of individuals of the same sex and similar age comprises measuring the expression level of the gene encoding SIRT2.

12. The method of claim 1, wherein the disease or condition is SLE.

13. The method of claim 1, wherein the disease or condition is cataracts.

14. The method of claim 1, wherein the disease or condition is osteoporosis.

* * * * *